United States Patent
Gillesberg

(10) Patent No.: US 8,020,435 B2
(45) Date of Patent: Sep. 20, 2011

(54) METHOD OF INVESTIGATING A COATED SURFACE OF AN OBJECT

(75) Inventor: Bo Gillesberg, Augustenborg (DK)

(73) Assignee: Danfoss A/S, Nordborg (DK)

( * ) Notice: Subject to any disclaimer, the term of this patent is extended or adjusted under 35 U.S.C. 154(b) by 747 days.

(21) Appl. No.: 11/914,846

(22) PCT Filed: May 18, 2006

(86) PCT No.: PCT/DK2006/000270
§ 371 (c)(1),
(2), (4) Date: Jul. 3, 2008

(87) PCT Pub. No.: WO2006/122559
PCT Pub. Date: Nov. 23, 2006

(65) Prior Publication Data
US 2008/0280027 A1   Nov. 13, 2008

(30) Foreign Application Priority Data
May 20, 2005   (DK) ................................. 2005 00739

(51) Int. Cl.
*G01N 37/00* (2006.01)
(52) U.S. Cl. ........................... 73/150 R; 118/712; 427/8
(58) Field of Classification Search ................. 73/150 R
See application file for complete search history.

(56) References Cited

U.S. PATENT DOCUMENTS
3,619,385 A   11/1971   Rjumshina et al.

FOREIGN PATENT DOCUMENTS
GB   2400113 A   10/2004
JP   57132045   8/1982
SU   473936   6/1975

OTHER PUBLICATIONS

PCT Search Report for Serial No. PCT/DK2006/000270 dated Aug. 30, 2006.
C.G. Granqvist, Electrochromic devices, Journal of the European Ceramic Society 25 (2005) 2907-2912.

*Primary Examiner* — Daniel Larkin
(74) *Attorney, Agent, or Firm* — McCormick, Paulding & Huber LLP

(57) ABSTRACT

A method of visually investigating a coated surface of an object, the coating comprising a metal or an alloy, in order to determine whether or not the coating is tight. An increasing potential is applied to the object until a desired current level has been obtained or until a maximum potential has been reached. In case the coating is tight this results in a change in color of the coating. This may be due to a polarization of the coating material and/or due to an increase in thickness of a naturally occurring metal oxide layer. In case the coating is tight the desired current level can not be obtained, and the potential is increased to the maximum level resulting in a change in color. In case pinholes are present it is possible to obtain the desired current level, and the increase in potential is stopped before it is high enough to cause the change in color. Provides a dramatic visual effect allowing an immediate determination of whether or not pinholes are present. Need for additional equipment for determining the presence of pinholes is avoided. In case the coating material is or comprises tantalum or an alloy of tantalum, the color is changed into a distinct blue color.

8 Claims, 1 Drawing Sheet

METHOD OF INVESTIGATING A COATED SURFACE OF AN OBJECT

CROSS REFERENCE TO RELATED APPLICATIONS

This application is entitled to the benefit of and incorporates by reference essential subject matter disclosed in International Patent Application No. PCT/DK2006/000270 filed on May 18, 2006 and Danish Patent Application No. PA 2005 00739 filed May 20, 2005.

FIELD OF THE INVENTION

The present invention relates to a method of investigating a coated surface of an object in order to determine whether or not the coated surface is tight, in particular in order to determine whether or not the coated surface comprises pinholes. More particularly, the present invention relates to an easy and visual method of determining whether or not pinholes are present in a coated surface of an object. The method of the present invention is particularly suitable for investigating objects having a coating of tantalum or an alloy of tantalum.

BACKGROUND OF THE INVENTION

For some applications it is desirable to provide a corrosive resistant coating to objects having an intended use in a relatively hostile and/or corrosive environment. This is, e.g., the case for objects which are used as implants. To this end coatings of refractory metals, such as niobium or tantalum, are frequently used on objects made from steel or other metals or alloys. Since a coating as described above will typically have a higher corrosion potential than the substrate material positioned below the coating, the coating will only eliminate corrosion if the coating is tight. If this is not the case, e.g. because the coating contains pinholes, there is a risk of pitting. Therefore, in order to obtain the desired corrosive resistant properties by means of the coating, it is necessary to ensure that the resulting coating is at least substantially tight, i.e. that it does not comprise any pinholes. One problem in this regard is that pinholes are usually very small, and it is therefore very difficult, or even impossible, to detect them visually.

Previously, coated surfaces have been investigated in order to detect possible pinholes by inserting the object in a circuit comprising a current source and an ammeter. If a reading can be obtained on the ammeter, the coated surface is conductive and thereby tight. This method is relatively time consuming and expensive since it requires the use of a current source and an ammeter each time it is desired to investigate whether or not the coating of an object is tight.

One method of investigating a coated surface in order to visually detect the presence of possible pinholes is described in JP 57132045. In the method disclosed in JP 57132045 a coated surface of a metallic material as a cathode opposite to an anode is positioned in an electrolyte containing a solution type electrochromic material, such as a viologen dye. A voltage is applied to the cathode, thereby causing an electrolytic reduction of the viologen dye from a colourless dication I to an insoluble monocation radical II. The insoluble monocation II is deposited in pinhole parts in a red or reddish purple colour. The presence or absence of pinholes is detected with an ammeter. At the same time, the places containing pinholes present a red or reddish purple colour, and therefore their position is distinctly known. The colour remains for a while, even after removal of the voltage, and can be returned to the original state when reverse voltage is applied after the inspection.

Thus, in the method disclosed in JP 57132045 the colouring of possible pinholes is obtained by deposition in the pinholes of a dye solved in an electrolyte. The resulting change in colour will, accordingly, only affect the actual areas of the pinholes. Since pinholes are by nature very small, it will be difficult to detect them purely by vision, even if they have been visually enhanced by deposition of the dye. In addition, the need for a measurement by means of an ammeter is still required in order to detect that pinholes are present, the visual inspection merely making it easier to determine the location of the pinholes which are known to be present following the ammeter measurement. Thereby the drawbacks of the method described above are not avoided in the method of JP 57132045. Furthermore, since the change in colour is obtained by deposition of a dye in the pinholes, there is a risk that some pinholes will not be marked by the dye, thereby creating a risk that such pinholes will go undetected in a subsequent visual inspection. This is highly undesirable.

SUMMARY OF THE INVENTION

It is, thus, an object of the present invention to provide a method of visually detecting possible pinholes in a coated surface of an object in a reliable manner.

It is a further object of the present invention to provide a method of investigating a coated surface of an object in which possible pinholes can be reliably detected in a purely visual manner.

It is an even further object of the present invention to provide a method for investigating a coated surface in which a dramatic visual effect is provided if the coating is tight or not tight.

It is an even further object of the present invention to provide a coated object allowing an end user to immediately determine whether or not the coating is at least substantially tight.

According to the present invention the above and other objects are fulfilled by providing a method of investigating a coated surface of an object, the coating material comprising a metal or an alloy, the method comprising the steps of:
applying an increasing potential to the object until a desired current level has been obtained or until a maximum potential has been reached,
visually inspecting the object, and
in case the colour of the coating has changed over at least a substantial part of the object, determining that the coating is at least substantially tight, or
in case the colour of the coating has not changed over at least a substantial part of the object, determining that the coating is not tight.

Since the colour of the coating changes over at least a substantial part of the object if the coating is at least substantially tight, a relatively dramatic visual effect is obtained. Thereby it is very easy to immediately determine by visual inspection whether or not the coating is tight. This is even possible for an end user of the object. Furthermore, the dramatic effect provides a very reliable detection of whether or not the coating is tight. Finally, the detection of the pinholes is purely visual, and the need for additional equipment is accordingly avoided.

The resulting object may advantageously be used in applications where it is important that the coating is tight. As mentioned above, this is, e.g., the case for objects which it is intended to position in highly corrosive environments. Implants are an example of such objects.

The change in colour or lack of change in colour is provided in the following manner. When applying an increasing potential to the object, it will be attempted to obtain the desired current level. If the coating is at least substantially tight it will not be possible to conduct a current of a sufficient current level because the tight coating is not conductive. Therefore the applied potential will continue to increase until the maximum potential is reached. The relatively high potential which is thereby applied to the object will cause the change in colour, thereby indicating that the coating is at least substantially tight. If, on the other hand, the coating is not tight, e.g. if the coating comprises one or more pinholes, the applied potential will result in a localized corrosion attack in the region(s) of the pinhole(s). Thereby it is possible to conduct a current at the desired current level. When this occurs the increase in potential will stop, and the applied potential will therefore not be sufficient to cause a change in colour.

The desired current level will depend on the total surface area of the object. However, the current density of the desired current is preferably within the interval $0.0001$ mA/cm$^2$ to $0.1$ mA/cm$^2$, preferably within the interval $0.001$ mA/cm$^2$ to $0.01$ mA/cm$^2$.

The maximum potential is preferably within the interval 10 V to 30 V, such as within the interval 15 V to 25 V, such as 16 V or 24 V.

The step of applying an increasing potential is preferably performed while the object is positioned in a liquid medium. The liquid medium may be any medium which the coating material is resistant in (i.e. the corrosion rate is less than 50 mpy (mils per year), preferably less than 2 mpy), and which has a conductivity of at least 10 S·cm$^2$, preferably at least 100 S·cm$^2$.

In one experiment a tantalum coated object having a total surface area of 800 cm$^2$ was positioned in a test solution of 1% sulphuric acid at room temperature. The object was connected to a power supply capable of providing maximum potentials of 16 V or 24 V. The applied potential was increased from 0 V in an attempt to let the voltage stabilise at a fixed current density of 0.005 mA/cm$^2$, corresponding to a current level of 4 mA. If this was not possible the applied potential was allowed to increase to the maximum value, i.e. 16 V or 24 V. The following was observed. For a tight coating and a maximum potential of 16 V the object turned brown after 5 minutes. For a tight coating and a maximum potential of 24 V the object turned blue after 5 minutes. For non-tight coatings containing one pinhole or three pinholes no change in colour was observed after 30 minutes.

The method is preferably performed at a temperature within the interval 0° C. to 120° C., such as within the interval 10° C. to 90° C., preferably at room temperature, i.e. approximately 20° C.

The step of applying an increasing potential to the object may be performed in such a way that the coating is at least partly polarized due to the high maximum potential if the coating is at least substantially tight, thereby causing the change in colour of the coating. The applied maximum potential should be sufficient to cause the desired change in colour when this polarization occurs, as described above. However, in case one or more pinholes are present in the coating, a selective corrosion of the underlying substrate material will occur, causing the coating to become conducting. It will therefore not be possible to obtain a sufficient overvoltage/potential to obtain a change in colour, and the colour of the object will therefore remain the original colour of the object, i.e. the natural colour of the coating material. Thereby the colour of the resulting object becomes an indicator for whether or not the coating was tight at the time the increasing potential was applied.

Alternatively or additionally, the step of applying an increasing potential to the object may cause an increase in thickness of a naturally occurring metal oxide layer on the coating, said increase in thickness in turn providing the change in the colour of the coating if the coating is at least substantially tight. In one embodiment the increase in thickness may be caused by a polarization of the coating as described above. Alternatively, the increase in thickness may result from a temperature effect or due to the object being positioned in an oxidizing medium. Such an increase in thickness of a metal oxide layer will, furthermore, be advantageous in case the coating layer is perforated at a later time, because the oxide layer has an insulating effect and prevents electrochemical half-reactions on the surface of the coating. Thereby galvanic (accelerated) corrosion of the substrate material will not be possible. Thus, if a change in colour has been obtained electrochemically as described, the corrosion rate will be reduced as compared to the corrosion rate of an uncoated object, even if the coating is no longer completely tight. This is a great advantage. Furthermore, an oxide layer of an increased thickness may provide the object with improved wear resistance and/or improved tribilogical properties.

The coating material may be or comprise a refractory metal or an alloy of a refractory metal, such as tantalum or an alloy of tantalum. Alternatively, the coating material could be or comprise any other suitable refractory metal, such as niobium, molybdenum, zirconium, tungsten or an alloy of one or more of these metals. Alternatively, the coating material may be or comprise any other suitable metal or alloy, e.g. titanium, as long as the coating is electrically conductive, and as long as it is possible to change the colour of the coating material by applying an increasing potential to the object. In case the coating material is or comprises tantalum or an alloy of tantalum, the change in colour will in most cases be such that the resulting object obtains a distinct blue colour if the coating is at least substantially tight.

The step of applying an increasing potential to the object may be performed by means of a galvanostat. Since a galvanostat is adapted to apply a specific current (as opposed to a specific voltage) this is very suitable in case a current of a predetermined level is desired as described above.

Preferably, the change in colour in case the coating is at least substantially tight is performed in an at least substantially permanent manner. The term 'at least substantially permanent' should in this context be interpreted as an effect which remains for a relatively long period of time, preferably until the outer layer is physically worn off. A substantially permanent effect is, e.g., obtained when the change in colour originates from a polarization of the coating material. When the changed colour remains at least substantially permanently it is immediately possible for an end user to determine whether or not the coating is at least substantially tight. As a side effect, when the change in colour is at least substantially permanent, the changes in the coating causing the change in colour will probably also be at least substantially permanent. Such changes will often have a beneficial effect on the corrosive properties of the object which will thereby be improved.

The invention further relates to an object having a coating, the colour of the coating being provided using the method described above. Since the colour of such an object reveals whether or not the coating is tight, an end user will be able to immediately see this, and thereby determine whether or not the object at hand has the desired corrosive resistant properties. Furthermore, as described above the object may further be at least partly protected from corrosion in case the coating is perforated at a later time.

BRIEF DESCRIPTION OF THE DRAWINGS

The invention will now be further described with reference to the accompanying drawings, in which.

DETAILED DESCRIPTION OF THE PREFERRED EMBODIMENT

Figure 1:
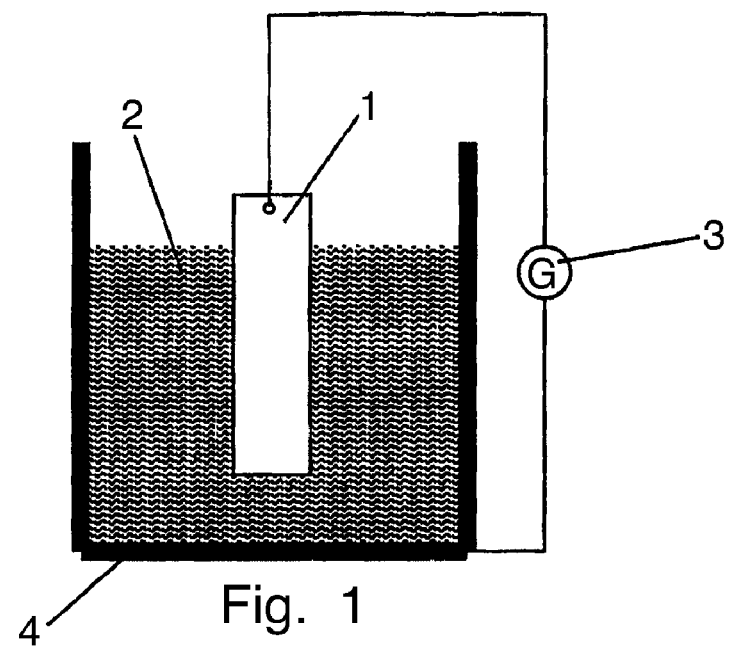
FIG. 1 is a schematic drawing of an object positioned in an electrolyte prior to applying an increasing potential to the object.

FIG. 1 is a schematic drawing of an object 1 which is positioned in an electrolyte 2. The object 1 is coated with a coating material comprising a metal or an alloy, and it is desired to investigate, in accordance with the present invention, whether or not the coating is tight. The object 1 is connected in series to a potential source 3 in the form of a galvanostat, which in turn is connected in series to the walls 4 of a container holding the electrolyte. When the potential source 3 is switched on, an increasing potential will be applied to the object 1 in an attempt to obtain a desired current level. If the coating is at least substantially tight, the coating will not be conductive, and it will therefore not be possible to obtain the desired current level. The potential will therefore continue to increase until a maximum potential is reached. This high potential causes the coating to become polarized, and as a result the colour of the coating will change.

Figure 2:
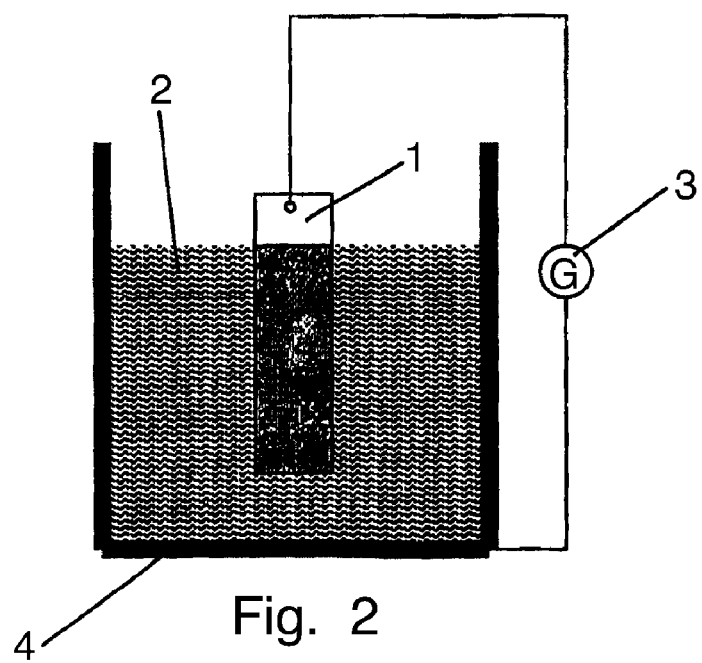
FIG. 2 is a schematic drawing of the object of FIG. 1 after an increasing potential has been applied to the object.

FIG. 2 is a schematic drawing of the object 1 of FIG. 1. However, in this case the potential source 3 has previously been switched on, and because the coating of the object 1 is at least substantially tight, the colour of the coating has changed as described above. If, on the other hand, the coating of the object 1 is not at least substantially tight, the coating will be conductive as previously explained, at it will therefore be possible to conduct a current at the desired current level. When this happens the increase in potential will be stopped, and the potential applied to the object 1 will therefore not be sufficient to cause a change in colour.

In case the coating of the object 1 comprises tantalum or an alloy of tantalum, the colour of the coating changes from grey to blue. Thereby it is very easy for an end user of the object 1 to determine whether or not the coating is at least substantially tight. If the object 1 appears blue, the coating is at least substantially tight, and if the object 1 appears grey the coating is not tight.

While the present invention has been illustrated and described with respect to a particular embodiment thereof, it should be appreciated by those of ordinary skill in the art that various modifications to this invention may be made without departing from the spirit and scope of the present invention.

What is claimed is:

1. A method of investigating a coated surface of an object, the coating material comprising a metal or an alloy, the method comprising the steps of:
   applying an increasing potential to the object until a desired current level has been obtained or until a maximum potential has been reached,
   visually inspecting the object, and
   in case the colour of the coating has changed over at least a substantial part of the object, determining that the coating is at least substantially tight, or
   in case the colour of the coating has not changed over at least a substantial part of the object, determining that the coating is not tight.

2. The method according to claim 1, wherein the step of applying an increasing potential to the object is performed in such a way that the coating is at least partly polarized if the coating is at least substantially tight, thereby causing the change in colour of the coating.

3. The method according to claim 1, wherein the step of applying an increasing potential to the object causes an increase in thickness of a naturally occurring metal oxide layer on the coating, said increase in thickness in turn providing the change in the colour of the coating if the coating is at least substantially tight.

4. The method according to claim 1, wherein the coating material comprises a refractory metal or an alloy of a refractory metal.

5. The method according to claim 4, wherein the coating material comprises tantalum or an alloy of tantalum.

6. The method according to claim 1, wherein the step of applying an increasing potential to the object is performed by means of a galvanostat.

7. The method according to claim 1, wherein the change in colour in case the coating is at least substantially tight is performed in an at least substantially permanent manner.

8. An object having a coating, the colour of the coating being provided using the method according to claim 1.

* * * * *